(12) United States Patent
Kravitz et al.

(10) Patent No.: US 8,828,034 B2
(45) Date of Patent: Sep. 9, 2014

(54) CANNULA

(75) Inventors: David Kravitz, Barrington Hills, IL (US); Christopher Steinman, Sandy, UT (US); David Pettinato, Schaumburg, IL (US)

(73) Assignee: Lifeline Scientific, Inc., Itasca, IL (US)

( * ) Notice: Subject to any disclaimer, the term of this patent is extended or adjusted under 35 U.S.C. 154(b) by 0 days.

(21) Appl. No.: 13/097,898

(22) Filed: Apr. 29, 2011

(65) Prior Publication Data

US 2012/0276519 A1 Nov. 1, 2012

(51) Int. Cl.
| | |
|---|---|
| *A61B 17/08* | (2006.01) |
| *A61M 5/00* | (2006.01) |
| *A01N 1/02* | (2006.01) |
| *A61B 17/122* | (2006.01) |
| *A61B 17/00* | (2006.01) |

(52) U.S. Cl.
CPC ..... *A61B 17/122* (2013.01); *A61B 2017/00969* (2013.01); *A01N 1/0247* (2013.01)
USPC .......................................... 606/158; 604/250

(58) Field of Classification Search
CPC ............... A01N 1/0247; A61B 17/122; A61B 2017/00969
USPC ................. 606/151, 157, 158, 218, 205–208; 604/246, 250; 24/133; 251/6, 7, 9, 10
See application file for complete search history.

(56) References Cited

U.S. PATENT DOCUMENTS

| | | | | |
|---|---|---|---|---|
| 678,943 | A | * | 7/1901 | Davis .............................. 128/885 |
| 1,339,419 | A | * | 5/1920 | Rea .............................. 24/135 K |
| 1,339,420 | A | * | 5/1920 | Rea .............................. 24/135 K |
| 1,566,653 | A | * | 12/1925 | Crotto .......................... 24/135 K |
| 2,262,162 | A | * | 11/1941 | Bock ............................. 24/134 P |
| 3,406,531 | A | | 10/1968 | Swenson et al. |
| 3,538,915 | A | | 11/1970 | Frampton et al. |
| 3,545,221 | A | | 12/1970 | Swenson et al. |
| 3,607,646 | A | | 9/1971 | de Roissart |
| 3,654,085 | A | | 4/1972 | Norr et al. |
| 3,660,241 | A | | 5/1972 | Michielsen |
| 3,777,507 | A | | 12/1973 | Burton et al. |
| 3,810,367 | A | | 5/1974 | Peterson |

(Continued)

FOREIGN PATENT DOCUMENTS

| | | |
|---|---|---|
| DE | 38 08 942 | 9/1989 |
| DE | 43 24 637 A1 | 3/1995 |

(Continued)

OTHER PUBLICATIONS

"Organ Preservation", J.H. Southard, Ph.D. and F.O. Belzer, M.D., *Principles of Organ Transplantation*, Chapter 10, pp. 194-215, 1989.

(Continued)

*Primary Examiner* — Julian W Woo
(74) *Attorney, Agent, or Firm* — Oliff PLC

(57) ABSTRACT

Disclosed is a cannula including a first clamping portion, a second clamping portion and a force applying portion configured to apply at least two different clamping forces across the first clamping portion and the second clamping portion when the cannula is in a closed state. The first clamping portion includes a first gear, the second clamping portion includes a second gear, and the first gear and the second gear are in meshing engagement.

29 Claims, 4 Drawing Sheets

(56) References Cited

U.S. PATENT DOCUMENTS

| | | | | |
|---|---|---|---|---|
| 3,843,455 | A | 10/1974 | Bier | |
| 3,866,611 | A * | 2/1975 | Baumrucker | 128/885 |
| 3,877,843 | A | 4/1975 | Fischel | |
| 3,881,990 | A | 5/1975 | Burton et al. | |
| 3,914,954 | A | 10/1975 | Doerig | |
| 3,935,065 | A | 1/1976 | Doerig | |
| 3,995,444 | A | 12/1976 | Clark et al. | |
| 4,006,744 | A | 2/1977 | Steer | |
| 4,186,565 | A | 2/1980 | Toledo-Pereyra | |
| 4,242,883 | A | 1/1981 | Toledo-Pereyra | |
| 4,462,215 | A | 7/1984 | Kuraoka et al. | |
| 4,471,629 | A | 9/1984 | Toledo-Pereyra | |
| 4,473,637 | A | 9/1984 | Guibert | |
| 4,474,016 | A | 10/1984 | Winchell | |
| 4,494,385 | A | 1/1985 | Kuraoka et al. | |
| 4,502,295 | A | 3/1985 | Toledo-Pereyra | |
| 4,723,974 | A | 2/1988 | Ammerman | |
| 4,745,759 | A | 5/1988 | Bauer et al. | |
| 4,766,740 | A | 8/1988 | Bradley et al. | |
| 4,800,879 | A | 1/1989 | Golyakhovsky et al. | |
| 4,837,390 | A | 6/1989 | Reneau | |
| 4,951,482 | A | 8/1990 | Gilbert | |
| 4,958,506 | A | 9/1990 | Guilhem et al. | |
| 5,004,457 | A | 4/1991 | Wyatt | |
| 5,141,847 | A | 8/1992 | Sugimachi et al. | |
| 5,157,930 | A | 10/1992 | McGhee et al. | |
| 5,184,629 | A * | 2/1993 | Erickson et al. | 128/885 |
| 5,209,747 | A * | 5/1993 | Knoepfler | 606/16 |
| 5,217,860 | A | 6/1993 | Fahy et al. | |
| 5,285,657 | A | 2/1994 | Bacchi et al. | |
| 5,326,706 | A | 7/1994 | Yland et al. | |
| 5,328,487 | A * | 7/1994 | Starchevich | 604/246 |
| 5,356,771 | A | 10/1994 | O'Dell | |
| 5,362,622 | A | 11/1994 | O'Dell et al. | |
| 5,383,854 | A | 1/1995 | Safar et al. | |
| 5,385,821 | A | 1/1995 | O'Dell et al. | |
| 5,425,705 | A * | 6/1995 | Evard et al. | 604/28 |
| 5,434,045 | A | 7/1995 | Jost | |
| 5,472,876 | A | 12/1995 | Fahy | |
| 5,536,251 | A * | 7/1996 | Evard et al. | 604/93.01 |
| 5,549,621 | A * | 8/1996 | Bessler et al. | 606/151 |
| 5,582,617 | A * | 12/1996 | Klieman et al. | 606/170 |
| 5,586,438 | A | 12/1996 | Fahy | |
| 5,632,746 | A | 5/1997 | Middleman et al. | |
| 5,653,721 | A * | 8/1997 | Knodel et al. | 606/151 |
| 5,681,740 | A | 10/1997 | Messier et al. | |
| 5,723,282 | A | 3/1998 | Fahy et al. | |
| 5,728,115 | A * | 3/1998 | Westcott et al. | 606/151 |
| 5,814,016 | A | 9/1998 | Valley et al. | |
| 5,821,045 | A | 10/1998 | Fahy et al. | |
| 5,856,081 | A | 1/1999 | Fahy | |
| 5,860,911 | A * | 1/1999 | Dolade Guardia | 600/39 |
| 5,928,264 | A * | 7/1999 | Sugarbaker et al. | 606/207 |
| 5,965,433 | A | 10/1999 | Gardetto et al. | |
| 6,046,046 | A | 4/2000 | Hassanein | |
| 6,138,678 | A * | 10/2000 | Nilsson | 128/885 |
| 6,355,010 | B1 | 3/2002 | Barbut | |
| 6,726,651 | B1 | 4/2004 | Robinson et al. | |
| 7,588,585 | B2 * | 9/2009 | Gold et al. | 606/206 |
| 7,641,671 | B2 * | 1/2010 | Crainich | 606/205 |
| 7,678,563 | B2 | 3/2010 | Wright et al. | |
| 2004/0221719 | A1 | 11/2004 | Wright et al. | |
| 2005/0165281 | A1 | 7/2005 | Ravikumar et al. | |
| 2006/0217746 | A1 * | 9/2006 | Krolman | 606/151 |
| 2007/0060939 | A1 | 3/2007 | Lancial et al. | |

FOREIGN PATENT DOCUMENTS

| | | |
|---|---|---|
| EP | 0 096 997 | 12/1983 |
| EP | 0 376 763 A2 | 7/1990 |
| JP | 2-258701 | 10/1990 |
| SU | 760972 | 9/1980 |
| WO | WO 91/03934 | 4/1991 |
| WO | WO 91/14364 | 10/1991 |
| WO | WO 93/00808 | 1/1993 |
| WO | WO 96/05727 | 2/1996 |
| WO | WO 96/13288 | 5/1996 |
| WO | WO 96/29865 | 10/1996 |
| WO | WO 96/30111 | 10/1996 |
| WO | WO 97/45527 | 12/1997 |
| WO | WO 99/15011 | 4/1999 |
| WO | WO 00/18226 | 4/2000 |
| WO | WO 02/26034 A | 4/2002 |
| WO | WO 2006/105444 A2 | 10/2006 |

OTHER PUBLICATIONS

"Organko Servierungsmachine OKM 82", Von Dietmer Scholz et al., East German Article, 1983 (with English Translation).

"Preservation of Cerebral Function During Circulatory Arrest and Resuscitation: Hypothermic Protective Considerations", Robert J. White, *Resuscitation*, vol. 1, pp. 107-115, 1972.

"Storage and Transport of Heart and Heart-Lung Donor Organs With Inflatable Cushions and Eutectoid Cooling", D.R. Wheeldon et al., *The Journal of Heart Transplaston*, vol. 7, pp. 265-268, 1988.

"MOX®-100 Renal Preservation System", Waters Instruments Medical Group, pp. 2-7, 1982.

"Organ Perfusion Systems: An Evaluation Criteria", Fereydoon Sadri, Ph.D., *T.O.P.S. Medical Corporation*, pp. 1-8, 1987.

Gauke Kootstra et al, "A New Device Towards Intermediate Term Kidney Preservation—An Experimental Study," 1980, pp. 86-89.

Jul. 4, 2012 International Search Report issued in International Application No. PCT/US2012/033244.

Jul. 4, 2012 Written Opinion issued in International Application No. PCT/US2012/033244.

Jul. 22, 2013 International Preliminary Report on Patentability issued in Application No. PCT/US2012/033244.

* cited by examiner

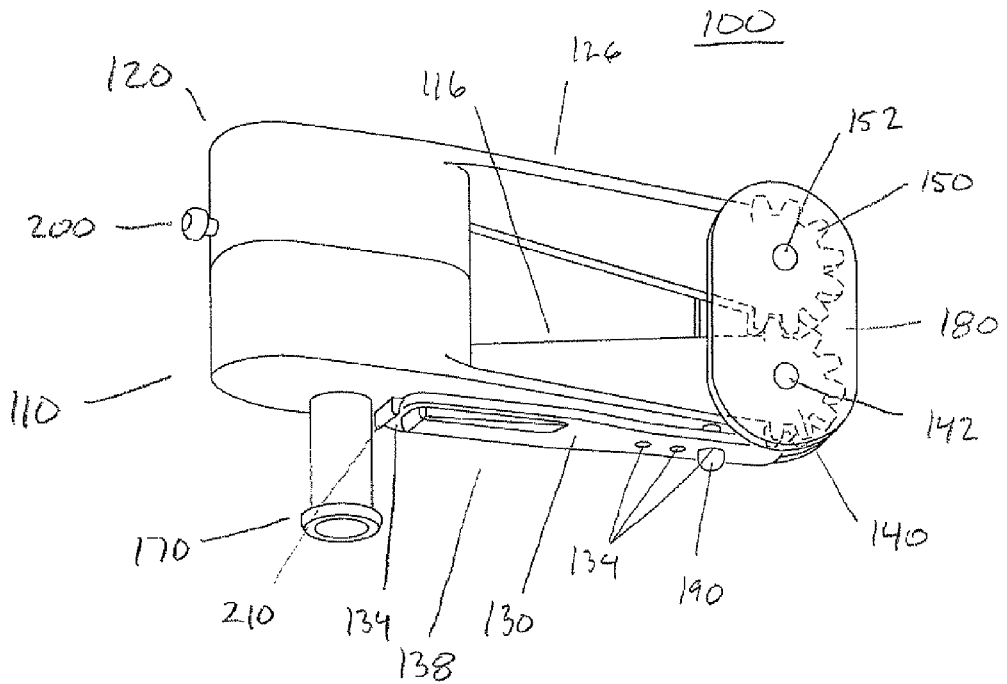
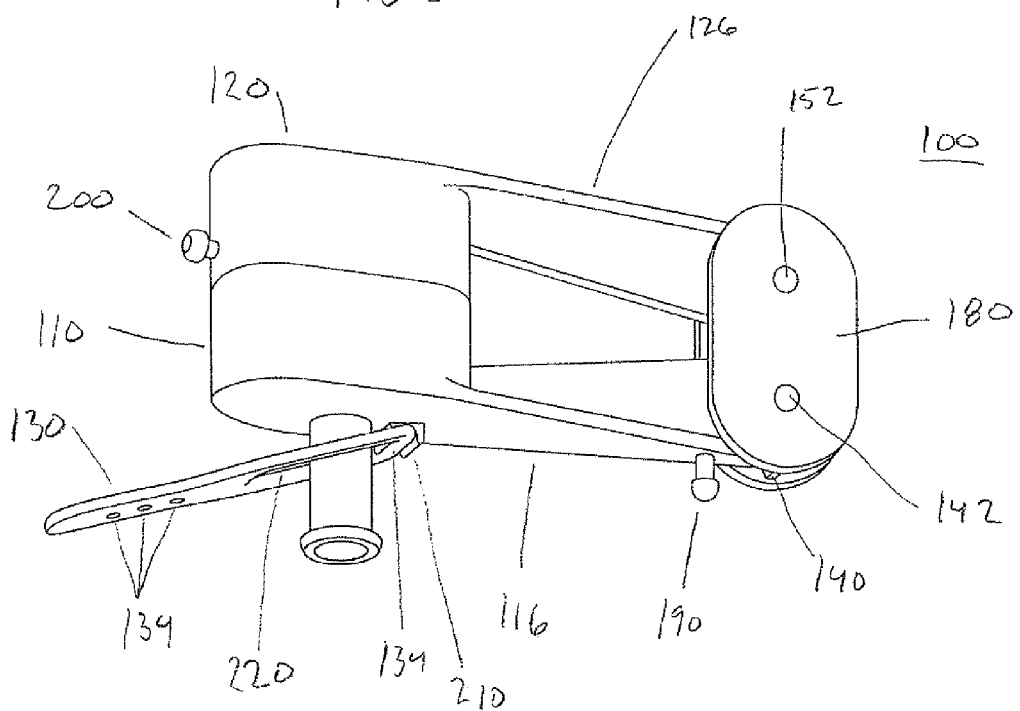

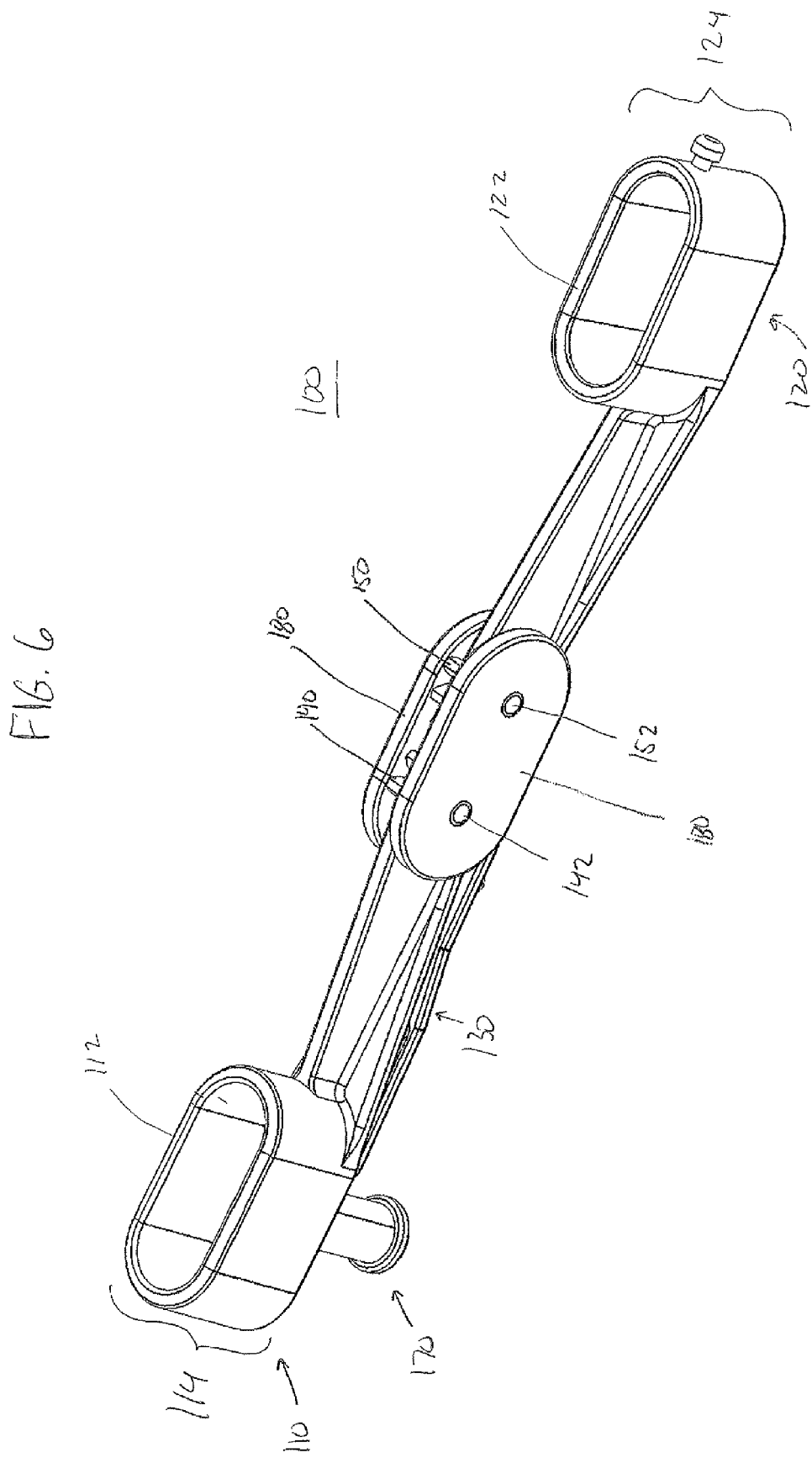

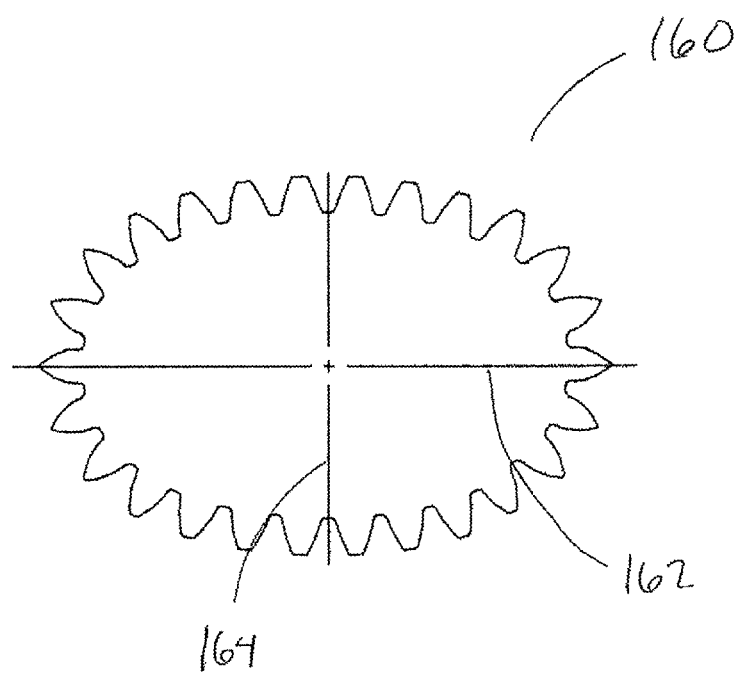

CANNULA

BACKGROUND

I. Related Technical Fields

Related technical fields include cannulas and clamping methods, and more specifically, cannulas and clamping methods for perfusing one or more organs to monitor, treat, sustain and/or restore the viability of the organ(s) and/or for transporting and/or storing the organ(s).

II. Related Art

Various devices have been developed that couple the anatomy of an organ being perfused to a machine or other equipment. Such devices are typically referred to as perfusion clamps or simply cannulas. Although the term cannula in general use has other meanings, the term cannula is used generically throughout the specification to refer to a clamp or other device that provides a connection through which a fluid flow may be established.

A type of cannula as described in U.S. Pat. No. 5,728,115 to Westcott et al., which is hereby incorporated by reference, is shown in FIGS. 1-3. A clamping device (cannula) 10 is used to couple the perfusion cannula to the renal aorta 34. The clamp 10 includes two longitudinal members 12 and 14 which pivot about a pin 16. The proximal end of the member 12 includes an integral handle 18, while the proximal end of the member 14 includes an integral handle 20. The distal end of the member 12 includes an elongated, hollow, annular, integral clamp head 24, while the distal end of the member 14 includes an elongated, hollow, annular, integral clamp head 26. Clamp head 26 includes a nipple 28 attached thereto. Movement of the handles 18 and 20 toward one another forces the members 12 and 14 to pivot about the pin 16, thereby forcing the clamp heads 24 and 26 of the members 12 and 14 away from one another. A spring 22 is positioned between the handles 18 and 20 in order to bias the handles apart. This, in turn, tends to force the clamp heads 24 and 26 together. Therefore, the clamp heads 24 and 26 of the distal ends of the members 12 and 14 are engaged in a clamping relationship unless an external compressive force is applied to the handles 18 and 20. A lumen 32 extends through the nipple 28.

In use, the clamp 10 is attached to the renal aorta 34 of a donor organ such as a kidney 36 by opening the clamp 10, passing the distal end 38 of the renal aorta 34 through the annular clamp head 24, holding the distal end 38 of the renal aorta 34 over the annular clamp head 24, and releasing pressure on the handles of the clamp 10 in order to allow the clamp head 26 to engage the distal end 38 of the renal aorta 34 against the annular clamp head 24. A catheter 40 may then be attached to the nipple 28 in order to provide perfusion of liquid through the lumen 32 and into the renal aorta 34

SUMMARY

The cannula shown in FIGS. 1-3 is not able to tune or adjust a force applied to clamped tissue. The resulting force may be excessive, which could result in damage to the tissue and subsequent loss of the tissue. In particular, excessive clamping force can result in damage to an interior surface of a clamped vasculature. Such damage can result in dislodged tissue or blood clots in a connected organ, which can damage the organ or result in a complete loss of the organ. Alternatively, the clamping force could be too low, resulting in leakage. The spring 22 does not allow for adjustment of a force applied by the cannula. Instead, the force applied will be a result of the thickness of clamped tissue, a corresponding displacement of spring 22, and a resultant force associated with that displacement. Similarly, if the tissue is relatively thin, the force applied may be too small to adequately secure the tissue to prevent leaking during perfusion.

Exemplary implementations of the broad inventive principles described herein provide a cannula having variable clamping force. Exemplary implementations provide first and second clamping portions and a force applying portion. The force applying portion is configured to be able to apply at least two different clamping forces across the first clamping portion and the second clamping portion when the cannula is in a closed state. Thus, an adjustable or tunable force can be applied to clamped tissue in order to avoid damage to the tissue or to increase clamping force, as necessary.

Exemplary implementations provide a force applying portion including an elastomeric material. The force applying portion stretches between the first clamping portion and the second clamping portion to retain the cannula in the closed state. Use of such a force applying portion allows for further tuning or adjustment of the force applied across the first clamping portion and the second clamping portion.

Exemplary implementations provide a force applying portion including at least three attachment points. The force applying portion is configured to apply at least two forces by using different combinations of two of the at least three attachment points. Use of such a force applying portion allows for further tuning or adjustment of the force applied across the first clamping portion and the second clamping portion.

Exemplary implementations provide a method of cannulating a vasculature. The method includes inserting the vasculature into a cannula; engaging at least one clamping surface of the cannula with the vasculature; selecting a clamping force from at least two clamping forces based upon the vasculature and an interaction between the vasculature and the cannula; and applying the force. The clamping force can be selected by choosing one of a plurality of connecting points to connect and secure a variable force applying member to the cannula. Such exemplary implementations address problems as discussed above.

The cannula shown in FIGS. 1-3 also cannot remain open without force being applied by a user, and is constructed to always tend towards a closed state. This is problematic in that a user must constantly apply force to keep the cannula open, which will occupy at least one of the users hands when ever the cannula is to be in an open state.

Exemplary implementations of the broad inventive principles described herein provide a cannula with a first clamping portion with a first gear, a second clamping portion with a second gear, and the first gear and the second gear are in meshing engagement. Choice of gears allows the cannula to tend to stay open or closed, depending on a position selected by a user. Gears can also be chosen to further tune the force applied by the force applying portion.

Exemplary implementations include the first gear as a first elliptical gear and the second gear as a second elliptical gear or only one of the first gear and the second gear as an elliptical gear. Use of elliptical gears provides an inflection point urging the cannula into an open state or a closed state depending on which side of the inflection point the gears are rotated. The gears can be driven away from the inflection point when a major axis of the first elliptical gear and a major axis of the second elliptical gear form a first angle less than 180°, which could correspond to the cannula being in a closed state, or a second angle greater than 180°, which could correspond to the cannula being in a fully open state. Alternatively, the first angle can be less than 135° and the second angle can be greater than 225°. These exemplary implementations provide for a cannula that does not always tend towards a closed state.

Exemplary implementations provide a force applying portion that is moveable from a force applying position to a standby position. The force applying portion does not apply any force across the first clamping portion and the second clamping portion when in the standby position. These exemplary implementations provide for a cannula that does not always tend towards a closed state.

Exemplary implementations provide the force applying portion to be lockable in a force applying position and a standby position. These exemplary implementations provide for a cannula that does not always tend towards a closed state. This is also advantageous in that the force applying portion can be retained in a manner that will not be in a user's way when not in a force applying position.

Exemplary implementations provide at least one of the first clamping portion and the second clamping portion with a tubing connection. The first clamping portion and the second clamping portion are configured to work in concert to hold vasculature in fluid communication with the tubing connection when the cannula is in the closed state. Preferably, the vasculature is held in sealed, leak free fluid communication with the tubing connection when the cannula is in the closed state.

Exemplary implementations provide a connecting member connecting the first clamping portion and the second clamping portion. The connecting member may connect to the first clamping portion at a first rotational axis of the first elliptical gear and connect to the second clamping portion at a second rotational axis of the second elliptical gear. The connecting member may include a first material with a first stiffness, at least one of the first clamping portion and the second clamping portion may include at least one second material with a second stiffness, with the first stiffness being lower than the second stiffness. These exemplary implementations provide for a cannula that does not always tend towards a closed state as well as allowing further tuning of the force applied by the force applying portion The cannula shown in FIGS. 1-3 is generally made of stainless steel or similar materials that can be sterilized and reused. This results in a cannula that is too expensive to procure and maintain.

Exemplary implementations of the broad inventive principles described herein provide a cannula that is disposable. Such an exemplary implementation solves the problem of the cannula shown in FIGS. 1-3 by reducing the procurement cost and eliminating cost associated with reuse.

The cannula shown in FIGS. 1-3 includes serrations or knurls (in clamp head 24 and/or clamp head 26) for securing tissue, and the serrations or knurls are designed for general purpose. Specific organs or tissues may require serrations or knurls that are specially designed for that organ or tissue or else the serrations or knurls may result in damage to the specific organs or tissues.

Exemplary implementations of the broad inventive principles described herein provide at least one of the first clamping portion and the second clamping portion with serrations and/or knurls configured to grasp a vasculature of a specific organ without damaging the vasculature. At least one of the first clamping portion and the second clamping portion may include an elastomeric material to operate in conjunction with and/or be substituted for the serrations and/or knurls. This avoids the above-described problem.

Exemplary implementations provide a first clamping portion and a second clamping portion that are plastic. Such an exemplary implementation addresses several of the above-described problems in that cost is reduced and the plastic can be chosen for use with a specific organ or tissue. This allows for choice of specific material properties that are compatible with, or do not incur damage to, the organ or tissue.

BRIEF DESCRIPTION OF THE DRAWINGS

Exemplary implementations can be described with reference to the following figures wherein:

FIG. 4 illustrates a cannula in a closed state;
FIG. 5 illustrates a cannula in another closed state;
FIG. 6 illustrates a cannula in an open state;
and
FIG. 7 illustrates an elliptical gear.

DETAILED DESCRIPTION OF EMBODIMENTS

Figure 1:
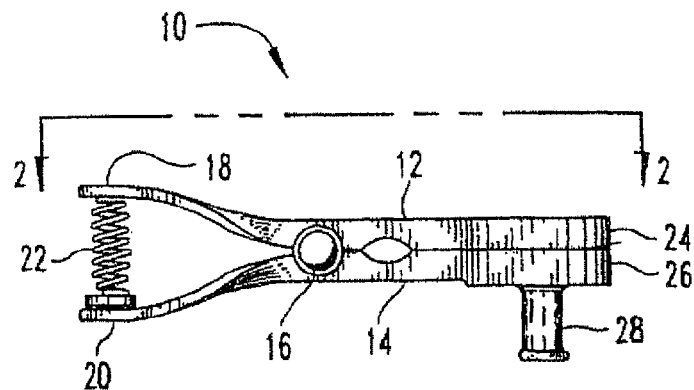
FIGS. 1-3 illustrate a cannula of the prior art.
Figure 2:
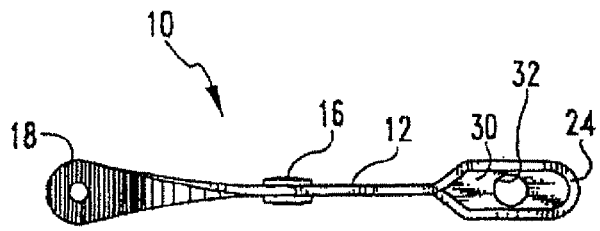
Figure 3:
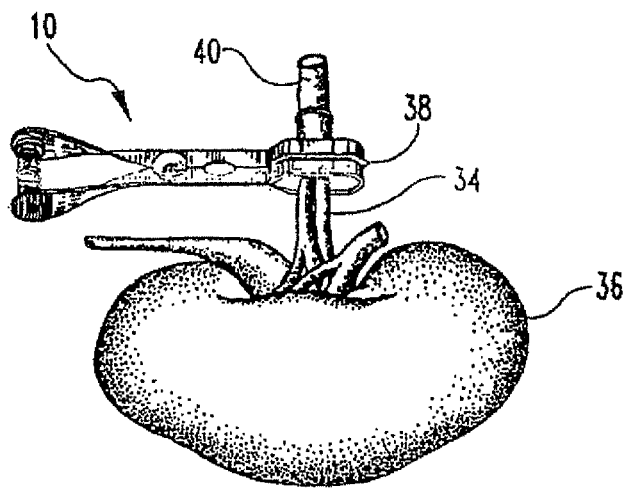

Preservation of organs by machine perfusion has been accomplished at hypothermic temperatures with or without computer control with crystalloid perfusates and without oxygenation. See, for example, U.S. Pat. Nos. 5,149,321, 5,395,314, 5,584,804, 5,709,654 and 5,752,929 and U.S. patent application Ser. No. 08/484,601 to Klatz et al., which are hereby incorporated by reference.

Ideally organs would be procured in a manner that limits their warm ischemia time to essentially zero. Unfortunately, in reality, many organs, especially from non-beating heart donors, are procured after extended warm ischemia time periods (i.e. 45 minutes or more). The machine perfusion of these organs at low temperature has demonstrated significant improvement (Transpl Int 1996 Daemen). Numerous control circuits and pumping configurations have been utilized to achieve this objective and to machine perfuse organs in general. See, for example, U.S. Pat. Nos. 5,338,662 and 5,494,822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thome et al.; U.S. Pat. Nos. 5,285,657 and 5,476,763 to Bacchi et al.; U.S. Pat. No. 5,157,930 to McGhee et al.; and U.S. Pat. No. 5,141,847 to Sugimachi et al., which are hereby incorporated by reference.

The cannulas and clamping methods described herein may be used in conjunction with apparatus and methods described in U.S. Pat. Nos. 6,014,864, 6,183,019, 6,241,945 and 6,485,450 to Owen, which are hereby incorporated by reference. While these apparatus and methods are related to organ recovery and transplantation, the cannulas and clamping methods described herein may also be used in various other medical procedures and with various other medical equipment where clamping with fluid flow is desired. Thus, the cannulas and clamping methods described herein are not limited to the applications described below in conjunction with the exemplary embodiments.

FIG. 4 shows a perfusion clamping apparatus or cannula 100 according to a first exemplary implementation. The cannula 100 is capable of connecting one or more arteries of an organ to a perfusion machine or system (not shown), for example, by connection to tubing of the perfusion machine or system. All medical fluid contact surfaces are preferably formed of or coated with materials compatible with the medical fluid used, preferably non-thrombogenic materials.

The medical fluid for perfusion may be any suitable medical fluid. For example, it may be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in tissue protection. Further, the medical fluid may also include blood or blood products.

The cannula 100 is shown in FIG. 4 in a closed or clamping condition and in FIG. 6 in an open condition. The cannula 100 comprises a first clamping portion 110, a second clamping portion 120, a force applying portion 130, a first gear 140, a second gear 150, a tubing connection 170, and connecting member 180. While the relative terms "first" and "second" are used to refer to the various portions as shown in the figures throughout this application, it should be understood that the various portions are referred to as "first" and "second" only to distinguish between similar structures in this description, and that the relative terms "first" and "second" are not limiting.

The force applying portion 130 as shown in FIG. 4 is in a standby position. The force applying portion 130 is fixed to the cannula by various attachment points 134 at a hinge 210 and a first button 190. The standby position is advantageous because the force applying portion 130 is kept out of a users way and locked until ready for use. In FIG. 5, the force applying portion is shown in an intermediate state between the standby position and a force applying position (not shown). In this intermediate state, the force applying member is attached to the cannula 100 at the hinge 210. In the force applying position, the force applying portion 130 is connected at the hinge 210 and a second button 200. In order to apply force in the force applying position, one of the attachment points 134 is connected to the second button 200 while the force applying portion remains connected at the hinge 210.

The force applying portion 130 is shown with an opening 220. As shown in FIG. 5, the opening 220 allows the force applying portion to be anchored or fixed at one end and to rotate over the tubing connection 170 and apply force equally on both sides of the tubing connection 170 when in the force applying position. In the force applying position, the force applying portion 130 wraps around or conforms to the shape of the cannula and attaches to the second button 200. This results in a force being applied across the first clamping portion 110 and the second clamping portion 120 that tends to keep the cannula in a closed state.

As shown in the exemplary implementation, three attachment points 134 can be fastened to the second button 200. Although three such attachment points 134 are shown, any number of attachment points (such as one, two, three, four, five, or more) fall within the broad inventive principles described herein. By including multiple attachment points 134 that can be fastened to the second button 200, the force applied by the force applying portion 130 can be selected and varied when the cannula 100 is in a closed state. Alternatively, a substantively same force can be applied to varying thicknesses of tissue if different thicknesses of tissue are to be clamped.

In one exemplary implementation, the force applying portion 130 is made from an elastomeric material 132. An elastomeric material 132 is advantageous in that it can be tailored with specific material properties to suit the needs of a user. Some material properties that may be important include bio compatibility and elasticity and compatibility with various terminal sterilization modalities. This may apply to all of the materials in this clamp. Elasticity can be chosen to tailor or fine tune the force applied by the force applying portion 130.

The force applying portion 130 can also be implemented in other ways while still meeting the broad inventive principles described herein. For example, the force applying portion could attach to the second clamping portion 120 at a first location, wrap around the first clamping portion 110, and attach to the second clamping portion 120 at a second location. The force applying portion 130 can include multiple separate structures to attach at multiple locations. The multiple separate structures can be chosen to tailor or fine tune the force applied by the force applying portion 130. The force applying portion 130 can also be one or more tension springs, which could be made from metal or other suitable materials.

Both of the first button 190 and the second button 200 are exemplary. Other structures could also be used, such as a hook, so long as attachment can be made with the force applying portion 130.

FIG. 6 shows a cannula 100 in an open state. The first clamping portion 110 includes a first head portion 114 and the second clamping portion 120 includes a second head portion 124. Each of the head portions is generally oval in shape. Other shapes will also meet the broad inventive principles described herein. For example, each of the head portions could be generally circular.

In the open state, a first clamping surface 112 and a second clamping surface 122 are visible. These clamping surfaces engage one another or a tissue disposed between the clamping surfaces when the cannula is in a closed position. The clamping surfaces may include one or more of serrations, knurls, and a soft, low durometer elastomer, to facilitate grasping tissue. If an elastomer is included, the durometer is preferably between about Shore-A 32 and about Shore-A 70.

The first head portion 114 is generally open on the side of the first clamping surface 112. As can be seen in FIG. 4, the side opposite the first clamping surface 114 includes a tubing connection 170. The tubing connection 170 includes an internal fluid passage to allow fluid communication with an internal space of the first head portion 114.

A second head portion 124 is open through a thickness to allow a tissue, such as a vasculature, to pass through from a side opposite the second clamping surface 122 and engage the second clamping surface 122.

FIG. 4 shows a first gear 140 and a second gear 150 in meshing engagement. One or both of the gears may be elliptical gears. The first gear 140 is attached to the first head portion 114 by a first beam 116. The second gear 150 is attached to the second head portion 124 by a second beam 126. The beams are shown with a generally T-shaped cross section, but any cross section can be chosen so long as it provides the appropriate mechanical properties. Including gears and attachments as disclosed allows for additional control of the clamping force.

The first gear 140 and the second gear 150 may be elliptical gears. With elliptical gears, the major axis of the ellipse can be oriented to provide advantageous effects. When the elliptical gears are in meshing engagement and the major axis of both elliptical gears are aligned, the gears will be at an inflection point. Such an inflection point will result in the gears tending to rotate away from the inflection point when an external force is applied. As such, the gears can be aligned to take advantage of this tendency. For example, if the major axis of the first gear 140 is at an angle of approximately 45° to a long direction of the first beam 116, and the second gear 150 is similarly positioned, the cannula 100 will tend towards either a closed (clamped) state as shown in FIG. 4 or a fully open state as shown in FIG. 6. A similar effect can be achieved if only one of the first gear 140 and the second gear 150 is an elliptical gear. FIG. 7 shows an example of an elliptical gear 160 with a major axis 162 and a minor axis 164.

A connecting member 180 attaches the first gear 140 and the second gear 150 at a first rotational axis 142 and a second rotational axis 152. If the gears are elliptical gears, the connecting member 180 will stretch as the elliptical gears near the inflection point. Similarly, if only one gear is elliptical, the connecting member will stretch as the elliptical gear rotates toward a position where the major axis is perpendicular to the mating gear. The amount of stretching, and therefore a force applied by the connecting member 180, will be greatest at the inflection point. The force applied will tend to urge the cannula 100 into either a closed or open state based upon which side of the inflection point the gears are oriented. In order to facilitate stretching of the connecting member 180, the connecting member can be made from an elastic material with appropriate material properties to fine tune or tailor the forces applied during use.

Portions of the cannula 100 can be made from any suitable materials, such as metal or clear or opaque plastic, but plastic provides several advantages. Plastic parts are usually less costly, and can therefore be made disposable. A disposable version of the cannula 100 will not have the additional costs associated with reuse, such as sterilization.

Portions of the cannula 100 can be made from optically clear material. This may be beneficial in that it can aid a clinician in positioning the vasculature and in detecting air bubbles or the interior or intima of the vasculature.

Either of the first clamping surface 112 and the second clamping surface 122 can include serrations and/or knurls to facilitate securing the clamped tissue. If the serrations or knurls are made from plastic, the plastic can be chosen with specific material properties to prevent damage to clamped tissue. Additionally, the serrations or knurls can be specifically tailored to the tissue to be clamped. Alternatively, the first clamping surface 112 and/or the second clamping surface 122 may include an elastomeric material to work in conjunction with and/or be substituted for the serrations and/or knurls.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:

1. A cannula comprising:
a first clamping portion;
a second clamping portion;
a tubing connection disposed on at least one of the first clamping portion and the second clamping portion and including an internal passage; and
a force applying portion configured to apply at least two different clamping forces across the first clamping portion and the second clamping portion when the cannula is in a closed state,
wherein the force applying portion is configured to rotate around the tubing connection, and the force applying portion is configured to bend in order to conform to a shape of the cannula when the cannula is in the closed state.

2. The cannula according to claim 1, wherein the first clamping portion comprises a first gear, the second clamping portion comprises a second gear, and the first gear and the second gear are in meshing engagement.

3. The cannula according to claim 2, further comprising a connecting member connecting to the first clamping portion at a first rotational axis of the first gear and connecting to the second clamping portion at a second rotational axis of the second gear.

4. The cannula according to claim 2, wherein the first gear comprises a first elliptical gear and the second gear comprises a second elliptical gear.

5. The cannula according to claim 4, wherein a major axis of the first elliptical gear and a major axis of the second elliptical gear form a first angle less than 180° in the closed state and form a second angle greater than 180° when the cannula is in a fully open state.

6. The cannula according to claim 5, wherein the first angle is less than about 135° and the second angle is greater than about 225°.

7. The cannula according to claim 1, wherein the first clamping portion and the second clamping portion are configured to work together to maintain vasculature in fluid communication with the tubing connection when the cannula is in the closed state.

8. The cannula according to claim 1, wherein: the force applying portion comprises an elastomeric material; and the force applying portion is configured to stretch between the first clamping portion and the second clamping portion to retain the cannula in the closed state.

9. The cannula according to claim 1, wherein: the force applying portion comprises at least three attachment points attachable to the cannula; and the force applying portion is configured to selectively apply one of the at least two forces depending on which two of the at least three attachment points are attached to the cannula.

10. The cannula according to claim 1, wherein the force applying portion is moveable from a force applying position to a standby position and the force applying portion does not apply any force across the first clamping portion and the second clamping portion when in the standby position.

11. The cannula according to claim 10, wherein the force applying portion is configured to be releasably fixed in the force applying position and the standby position.

12. The cannula according to claim 1, further comprising a connecting member connecting the first clamping portion and the second clamping portion.

13. The cannula according to claim 12, wherein: the connecting member comprises a first material with a first stiffness; at least one of the first clamping portion and the second clamping portion comprise at least one second material with a second stiffness; and the first stiffness is lower than the second stiffness.

14. The cannula according to claim 1, wherein at least one of the first clamping portion and the second clamping portion comprises a grasping surface configured to grasp vasculature of a specific organ without damaging the vasculature.

15. The cannula according to claim 14, wherein the grasping surface comprises at least one of serrations, knurls, and an elastomeric material.

16. The cannula according to claim 1, wherein the first clamping portion and the second clamping portion comprise a plastics material.

17. The cannula according to claim 1, wherein the force applying portion is configured to selectively apply one of the at least two different clamping forces.

18. The cannula according to claim 1, wherein the force applying portion comprises: an anchor attachment point; and at least two force determining attachment points; wherein: the force applying portion is configured to be attached to the cannula by the anchor attachment point and one of the at least two force determining attachment points.

19. The cannula according to claim 18, wherein the one of the at least two force determining attachment points is determinative of which of the at least two different clamping forces is applied across the first clamping portion and the second clamping portion.

20. The cannula according to claim 1, wherein the force applying portion is tensioned when the cannula is in the closed state and the force applying portion applies a clamping force.

21. The cannula according to claim 1, wherein the force applying portion is configured to rotate over the tubing connection such that the tubing connection is disposed through the force applying portion when the cannula is in the closed state.

22. A cannula comprising:
   a first clamping means for clamping vasculature of an organ;
   a second clamping means for clamping the vasculature of the organ;
   a tubing connection means disposed on at least one of the first clamping means and the second clamping means and including an internal passage; and
   a force applying means for applying at least two different clamping forces across the first clamping means and the second clamping means when the cannula is in a closed state,
      wherein the force applying means is configured to rotate around the tubing connection means, and the force applying means is configured to bend in order to conform to a shape of the cannula when the cannula is in the closed state.

23. A cannula comprising:
   a first clamping portion comprising a first gear;
   a second clamping portion comprising a second gear in meshing engagement with the first gear; and
   a tubing connection disposed on at least one of the first clamping portion and the second clamping portion and including an internal passage,
      wherein a force applying portion of the cannula is configured to rotate around the tubing connection, and the force applying portion is configured to bend in order to conform to a shape of the cannula when the cannula is in a closed state.

24. The cannula according to claim 23, further comprising a connecting member connecting to the first clamping portion at a first rotational axis of the first gear and connecting to the second clamping portion at a second rotational axis of the second gear.

25. The cannula according to claim 23, wherein the first gear comprises a first elliptical gear and the second gear comprises a second elliptical gear.

26. The cannula according to claim 25, wherein a major axis of the first elliptical gear and a major axis of the second elliptical gear form a first angle less than 180° in the closed state and form a second angle greater than 180° when the cannula is in a fully open state.

27. The cannula according to claim 23, wherein one of the first gear and the second gear is an elliptical gear.

28. The cannula according to claim 23, wherein the at least one gear is in meshing engagement with a second gear.

29. A cannula comprising:
   a first clamping portion;
   a second clamping portion;
   a tubing connection disposed on the first clamping portion and including an internal passage; and
   a force applying portion configured to apply at least two different clamping forces across the first clamping portion and the second clamping portion when the cannula is in a closed state,
      wherein the force applying portion applies force substantially equally on opposing sides of the tubing connection, wherein the opposing sides are disposed on a surface on the first clamping portion.

* * * * *